United States Patent [19]

Bradley et al.

[11] Patent Number: 4,577,514
[45] Date of Patent: Mar. 25, 1986

[54] METHOD AND APPARATUS FOR SAMPLING LIQUID PHASE COMPONENTS FROM A LIQUID-SEMISOLID FLUID

[75] Inventors: Charles A. Bradley, Brentwood; Herman Benge, Nashville; Fritz F. Parl, Nashville; William R. Seebaugh, Nashville, all of Tenn.

[73] Assignee: Vanderbilt University, Nashville, Tenn.

[21] Appl. No.: 598,074

[22] Filed: Apr. 9, 1984

[51] Int. Cl.⁴ .................. G01N 1/18; G01N 33/48
[52] U.S. Cl. .................. 73/863.01; 73/301; 73/863.21; 422/101; 436/177; 604/414
[58] Field of Search .................. 604/158, 411, 414; 128/201, 764; 73/863.01, 863.21, 727, 301, 299; 436/177, 150, 63; 422/101

[56] References Cited

U.S. PATENT DOCUMENTS

| | | | |
|---|---|---|---|
| 2,630,803 | 3/1953 | Baran | 604/158 |
| 3,550,583 | 12/1970 | Chiku et al. | 73/727 X |
| 3,654,579 | 4/1972 | Kurtz et al. | 73/727 X |
| 3,840,008 | 10/1974 | Noiles | 604/158 X |
| 3,896,810 | 7/1975 | Akiyama | 604/158 X |
| 4,116,066 | 9/1978 | Mehl et al. | 604/414 X |
| 4,335,608 | 6/1982 | Wood et al. | 73/301 |
| 4,368,639 | 1/1983 | Owens | 73/301 |
| 4,487,836 | 12/1984 | Takayanagi et al. | 436/150 X |

FOREIGN PATENT DOCUMENTS

| | | | |
|---|---|---|---|
| 0039184 | 4/1978 | Japan | 73/863.01 |
| 0147630 | 9/1983 | Japan | 356/246 |

Primary Examiner—Arnold Turk

[57] ABSTRACT

To sample liquid phase components of a biological fluid which has been subjected to centrifugation to separate its liquid and semisolid phase components and define a liquid-semisolid interface therebetween, a probe carrying a sensor at its end is extended into and through the liquid phase components until the sensor detects the interface, whereupon further extension of the probe into the fluid is halted. A sample of liquid phase components is then withdrawn through openings in the probe spaced from the interface, so that only liquid components are sampled. It is contemplated that a stopper close a vessel containing the biological fluid, and that the probe be extended through and movable within a needle which first pierces the stopper, so that the probe may be moved through the needle and into the vessel. It is also contemplated that the withdrawn liquid phase components be aseptically transferred to a receiving vessel, and that the probe be cleansed with a flushing solution between sampling operations.

19 Claims, 9 Drawing Figures

METHOD AND APPARATUS FOR SAMPLING LIQUID PHASE COMPONENTS FROM A LIQUID-SEMISOLID FLUID

BACKGROUND OF THE INVENTION

The present invention relates to an improved method of and apparatus for isolating liquid phase components from semisolid phase components of a biological fluid.

A conventionally employed technique for separating liquid phase components from semisolid phase components of a blood mixture utilizes centrifugation of the mixture. The serum or plasma is generally then isolated from the semisolid portion by pipette or decantation procedures. Because of the agitation to which the sample is subjected by the procedures, it often happens that some semisolid phase components enter the liquid phase components, and the method does not entirely separate all particulate matter from the desired serum or plasma. When the serum is to be subjected to diagnostic analysis with, for example, an automated electronic analyzer, it is important to employ a particulate-free specimen. Fibrin fibers are often the cause of analyzer malfunctions when they clog conduits or orifices in the analyzer.

To improve the quality of serum samples obtained using conventional procedures, blood component separation devices have been developed, such as those described in U.S. Pat. Nos. 3,481,477, 3,512,940 and 3,693,804. Although such devices isolate the desired blood serum or plasma from the semisolid portion of the sample, they are relatively expensive to construct, and as a result have not been as widely accepted commercially as the need suggests. In addition, blood component separation devices such as those described in the above patents, operate in part by exerting force or pressure upon the blood mixture to be separated. If too great a force is imposed upon the mixture, there is a danger that the serum or plasma will pass through the devices with sufficient velocity to force particulate matter into the serum portion. The isolation procedure with the devices is also usually carried out following separation of the blood components by centrifugation, which requires two distinct steps and consequent extension of time required for total serum preparation.

To avoid the increased time and expense required to use such blood component separation devices, as well as the potential for contamination of the serum portion with particulate matter, it would be desirable to provide some means for automatically obtaining a pure serum sample wherein, after centrifugation of the blood mixture, there exists between the liquid and semisolid phase components only a liquid-semisolid interface of serum and cell coagulum or a relatively inexpensive silicone separation barrier. Unfortunately, although the art provides various types of automated fluid samplers, none has been found suitable for the purpose.

One prior type of automated fluid sampler is described in U.S. Pat. No. 4,325,909, in which a vertically and horizontally movable arm structure has a fluid probe at its distal end for fluid sampling and transfer. The vertical position of the arm and probe are controlled by an electrical liquid level sensing circuit, such that upon movement of the probe toward and to the liquid sample, when the probe touches the surface of the sample a circuit is established to then further move the probe to a preselected fixed depth in the liquid. In consequence, since the vertical position of the liquid-semisolid interface of a blood mixture varies from sample to sample, the device is not entirely suitable for sampling the serum portion of a blood mixture, since for the purpose the probe should extend closely to but not beyond the interface, so that substantially all of the serum, but not particulate matter, is sampled.

Another automated apparatus for analyzing liquids is taught by U.S. Pat. No. 3,549,330, wherein a liquid sample is maintained in an airtight container while being moved from station to station and while necessary liquids are supplied to and removed from the container. However, the probe for removing and adding liquids is fixed for movement between a predetermined lowered position for removing or supplying liquid and a raised position for permitting rotation of a container tray and advancement of the next container to the operating station. Again, because the vertical position of the liquid-semisolid interface of a blood mixture varies from mixture to mixture, movement of the probe between fixed vertical positions makes this apparatus also less than entirely suitable for blood serum sampling, since there is no way to variably control proper positioning of the probe during sampling.

OBJECTS OF THE INVENTION

An object of the present invention is to provide a serum sampler for a blood mixture which has been subjected to centrifugation, wherein a probe is extended into the serum and its end is automatically positioned at a selected location with respect to an interface between the serum and cell coagulum, for aspiration of a substantially particulate-free serum through openings in the probe which are spaced above the interface.

Another object is to provide such a sampler, wherein the probe is extended into the serum until its distal end just reaches the interface.

A further object is to provide such a sampler, wherein the probe carries at its distal end a sensor for detecting contact of the distal end with the interface to terminate further extension of the probe into the mixture.

Yet another object is to provide such a sampler, wherein the sensor is a pressure transducer for generating an electrical signal to terminate further movement of the probe upon its distal end encountering the interface.

A still further object is to provide such a sampler, wherein the probe is vertically movable through a needle which first pierces a stopper on a vessel in which the mixture is contained, to enable extension of the probe through the stopper and into the vessel.

SUMMARY OF THE INVENTION

In accordance with the present invention, an apparatus for isolating liquid phase components from semisolid phase components of a fluid mixture of the type in which the liquid phase components overlie the semisolid phase components and a liquid-semisolid interface is defined therebetween, comprises a probe; means for moving said probe into and through the liquid phase components and toward and to the interface; and means for sensing when an end of said probe reaches the interface and for generating a signal in response thereto. Means are provided for automatically terminating movement of said probe upon generation of said signal, said probe has an opening therein toward said end thereof and said opening is located close to but spaced from the interface and entirely in the liquid phase components when said end reaches said interface, and means is included for withdrawing liquid phase components through said opening and probe after termination of movement of said probe, whereby only liquid phase, particulate-free components are withdrawn from the mixture.

The invention also contemplates a method of isolating liquid phase components from semisolid phase components of a fluid mixture of the type in which the liquid phase components overlie the semisolid phase components and a liquid-semisolid interface is defined therebetween, which comprises the steps of moving a probe into and through the liquid phase components and toward and to the interface; sensing when an end of the probe reaches the interface and generating a signal in response thereto; interrupting said moving step upon occurrence of said signal generating step and, after occurrence of said interrupting step, withdrawing liquid phase components through an opening in the probe close to but spaced from the interface and positioned entirely within the liquid phase components when the probe reaches the interface.

The foregoing and other objects, advantages and features of the invention will become apparent upon a consideration of the following detailed description, when taken in conjunction with the accompanying drawings.

BRIEF DESCRIPTION OF THE DRAWINGS

FIGS. 2-6 show sequential stages of operation of the apparatus in withdrawing the liquid phase components;

FIG. 7 is an enlarged, fragmentary view of a distal end of a probe or aspirator tube of the apparatus, illustrating a sensor within the end for detecting a liquid-semisolid interface of the blood mixture upon movement of the distal end thereagainst.

DETAILED DESCRIPTION

Figure 1:
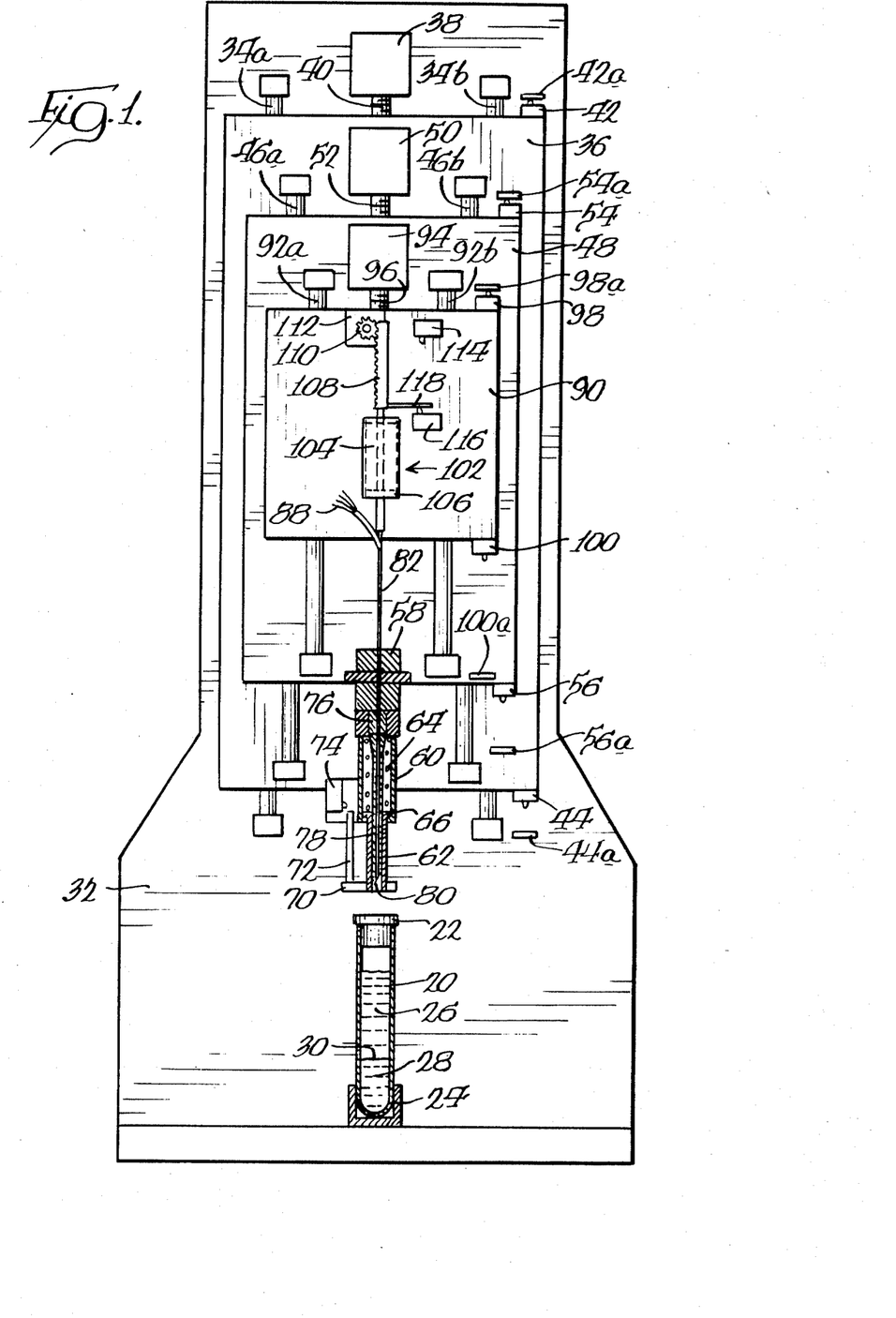
FIG. 1 is a front elevation view, partly in cross section, illustrating a sampling apparatus, constructed according to the teachings of the invention, for withdrawing liquid phase components from a centrifuged blood mixture.

Referring to FIG. 1, the invention provides a method of and an apparatus for isolating the liquid phase components, serum or plasma of a biological fluid, such as a blood mixture, from the solid phase components to obtain a sample of the serum. The blood mixture is aseptically contained in a test tube 20 closed by a stopper 22 and supported upright beneath the apparatus in a rack 24. To the extent conventional, prior to sampling the serum the blood mixture is subjected to centrifugation, so that serum 26 then overlies solid phase components or cell coagulum 28 and the components define a liquid-semisolid interface 30 therebetween. Although the interface is shown at a juncture between serum and cell coagulum, if a serum separation tube of a type sold by Monoject, a Division of Sherwood Medical, under the trademark CORVAC or by Becton-Dickinson under the trademark SST were used, then after centrifugation a silicone separation barrier would be between the serum and cell coagulum, and the interface 30 would be defined at the juncture of the serum and silicone separation barrier.

The sampling apparatus comprises a stationary support 32 having a pair of rods 34a and 34b received within sleeves (not shown) on a rear side of a first plate 36 to mount the plate for vertical movement on the support. To move the plate, a first reversible electric motor 38 on the support has on its output shaft a lead screw 40 which meshes with a threaded member (not shown) on the back of the plate. Limit switches 42 and 44 for the motor are on the plate and have associated triggers 42a and 44a on the support, the positions of which triggers control the extent of vertical movement of the plate on the support.

The first plate 36 in turn has a pair of rods 46a and 46b received within sleeves (not shown) on a back side of a second plate 48 to mount the second plate for vertical movement on the first. To move the second plate a second reversible electric motor 50 on the first plate has on its output shaft a lead screw 52 which meshes with a threaded member (not shown) on a rear side of the second plate. Limit switches 54 and 56 for the motor are on the second plate and have associated triggers 54a and 56a on the first plate, the positions of which triggers determine the extent of vertical movement of the second plate on the first.

Carried at the bottom of the second plate 48 is a tube sensor and stopper penetrator assembly mounting member 58 having a vertically extending passage centrally therethrough. With reference also to FIG. 2, a generally cylindrical tube sensor guide 60 extends downwardly from the mounting member, and received for reciprocation in the guide is a generally cylindrical tube sensor 62. A compression spring 64 within the guide engages a radially outwardly extending flange 66 at the top of the tube sensor to normally urge the tube sensor downwardly and outwardly of the guide, and a radially inwardly extending flange 68 at the lower end of the guide retains the tube sensor within the guide. A foot 70 at the bottom of the tube sensor carries an upwardly extending trigger 72 which is adapted, as will be described, to actuate a limit switch 74 to control energization of the motor 38.

Figures 6, 7:
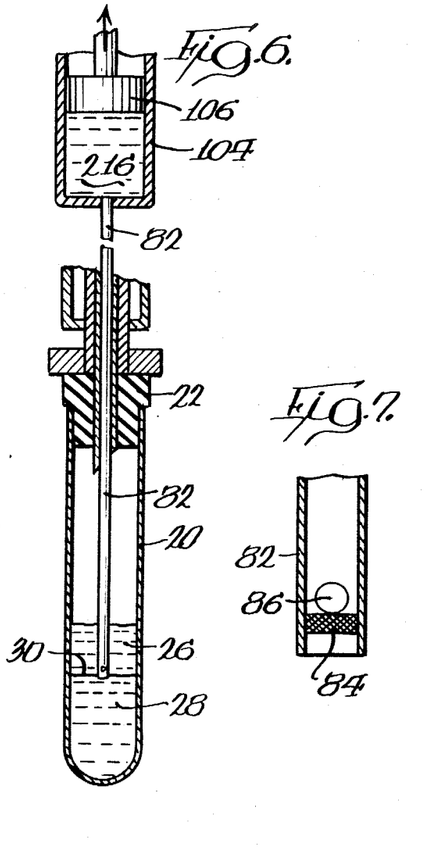

A Luer lock 76 is centrally within a lower end of the mounting member 58, and supports a stopper piercing or puncturing needle 78 which extends downwardly through the tube sensor guide 60, the tube sensor 62 and the spring 64 and terminates in a sharp, pointed end 80. Extending centrally through and slidably movable for reciprocation within the mounting member, the Luer lock and the needle is a tubular serum sampling probe or aspirating tube 82. With reference also to FIG. 7, a lower or distal end of the probe is closed by a sensor 84 fastened within a passage therethrough, for example by epoxy, about 0.01" inwardly of the end, and formed through the probe just above the sensor are one or more openings 86. The sensor is preferably an electromechanical pressure transducer of a type described in U.S. Pat. No. 3,654,579, the teachings of which are specifically incorporated herein by reference, and comprises four piezo-resistive sensing elements diffused in a diaphragm in a Wheatstone bridge configuration and adapted to generate electrical signals in response to sensed pressure changes. A plurality of conductors 88 connected to the sensor extend upwardly through the probe and exit through an appropriately sealed opening.

The remaining mechanical structure of the sampling apparatus comprises a third plate 90, mounted for vertical movement along a pair of rods 92a and 92b on the second plate 48. The third plate is moved by a third reversible electric motor 94 on the second plate, which carries on its output shaft a lead screw 96 engaged with a threaded member (not shown) on the back of the third plate. Limit switches 98 and 100 on the plate control energization of the motor, and have associated triggers 98a and 100a on the second plate, the positions of which triggers determine the maximum extent of vertical movement of the third plate on the second.

Carried by the third plate 90 is a serum sample collecting chamber or syringe, indicated generally at 102, which comprises a cylinder 104 on the plate and a plunger 106 reciprocable therein by a rack 108 meshed with a pinion 110 on the output shaft of a fourth reversible electric motor 112. A pair of limit switches 114 and 116 control energization of the motor in response to contact therewith by a trigger 118 carried by the rack, and the upper end of the probe 82 is securely attached to the third plate and couples with an inlet to the cylinder. The limit switch 116 deenergizes the motor when the plunger is driven to the bottom of the cylinder, and the limit switch 114 is adjustable on the plate to control the extent of upward movement of the plunger, and therefore the volume of a serum sample.

Figure 8A:
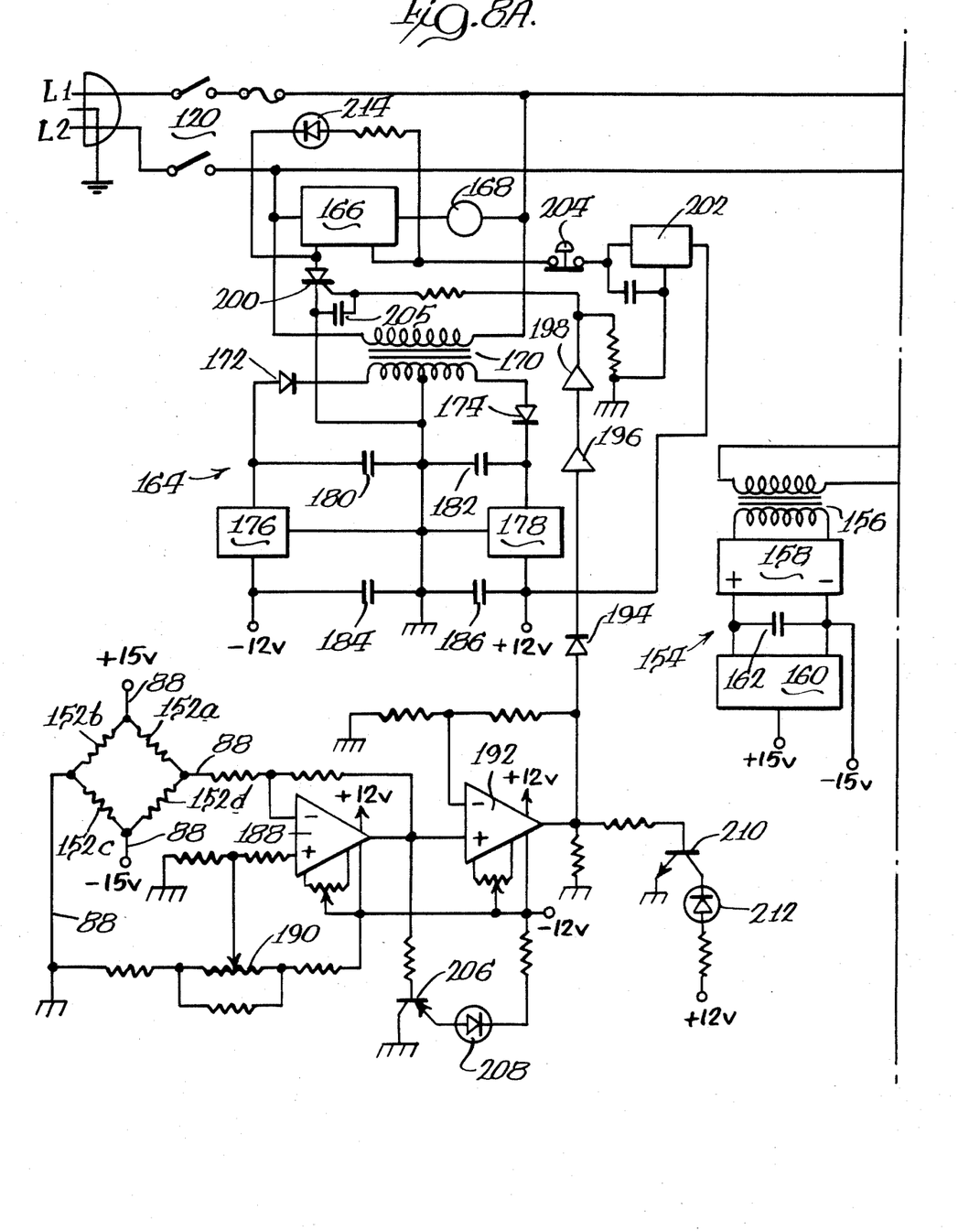
FIGS. 8A and 8B schematically represent a circuit for controlling operation of the apparatus.
Figure 8B:
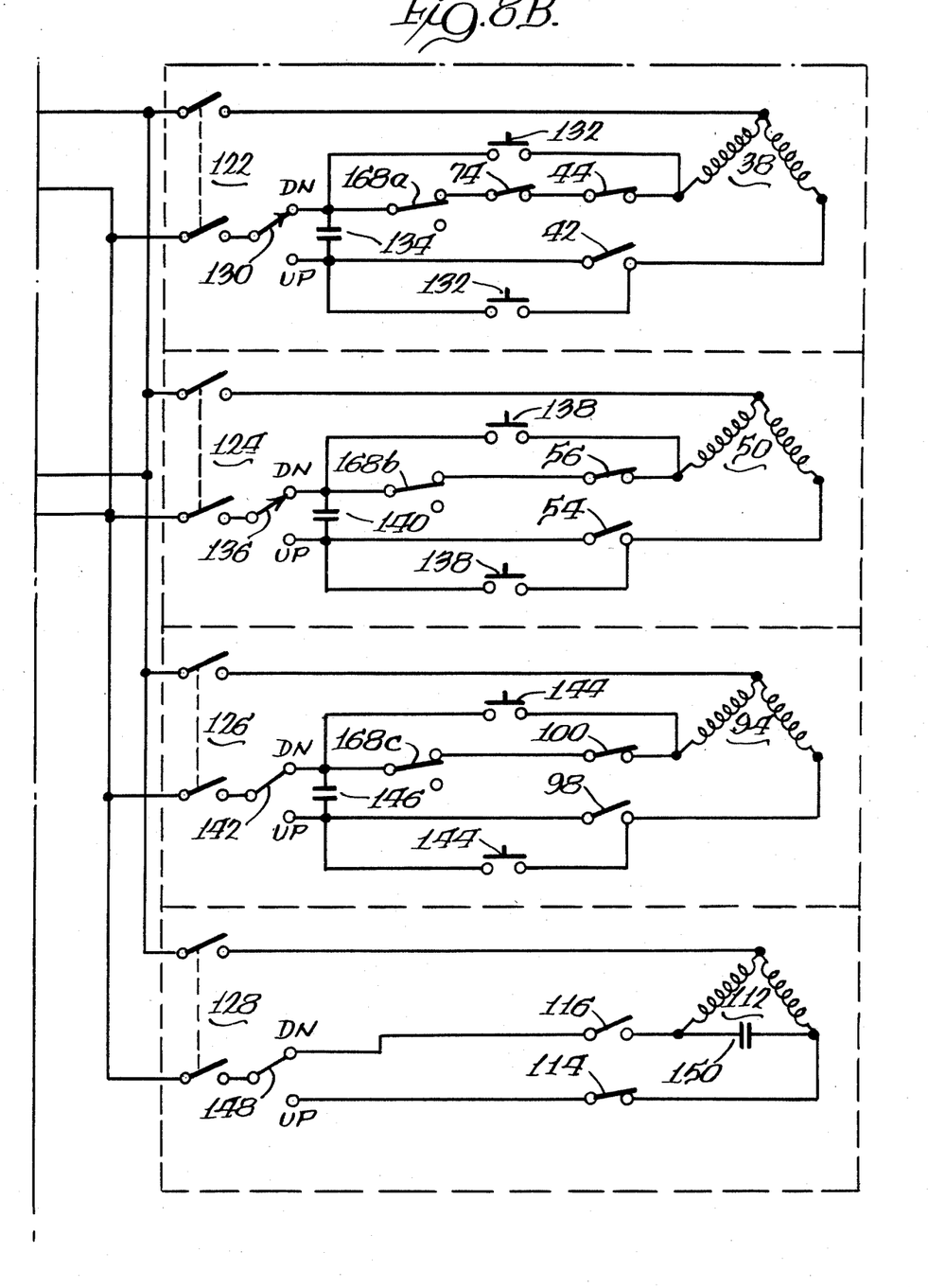

FIGS. 8A and 8B illustrate a circuit for controlling operation of the apparatus, with the limit switches having states for the orientation of the apparatus as shown in FIG. 1, which is as of the beginning of a sampling cycle. The circuit has a main power switch 120 for connecting power with switches 122, 124, 126 and 128 of circuits for controlling the respective motors 38, 50, 94 and 112. The circuit for the motor 38 includes the limit switches 42, 44 and 74, and up/down switch 130, a switch 132 and a capacitor 134. With the first plate 36 in its upper position, to drive it downwardly the switch 122 is closed, the up/down switch is placed in the "down" position and the switch 132 is momentarily actuated to operate the motor 38 and lower the plate. When the plate begins to move down the limit switch 42 closes, whereupon the switch 132 may be released and downward movement will continue until one of the limit switches 44 and 74 opens. To return the plate to its elevated position, the up/down switch is moved to the "up" position and the switch 132 is again momentarily actuated, whereupon the motor 38 drives the plate up until the limit switch 42 opens.

The circuit for the motor 50 which drives the second plate 48 includes the switch 124, the limit switches 54 and 56, an up/down switch 136, a switch 138 and a capacitor 140. The circuit for controlling the motor 94 which drives the third plate 90 is similar, and includes the switch 126, the limit switches 98 and 100, an up/down switch 142, a switch 144 and a capacitor 146. To drive either plate downwardly, its associated up/down switch is placed in the "down" position and its switch 138 or 144 is momentarily actuated, with the down limit switch 56 or 100 then controlling the extent of downward movement. To drive either plate upwardly, its associated up/down switch is placed in the "up" position and its switch 138 or 144 is momentarily actuated, with the up limit switch 54 or 98 then limiting the extent of upward movement.

The circuit for the sample collecting chamber or syringe motor 112 includes the switch 128, the limit switches 114 and 116, an up/down switch 148 and a capacitor 150. The capacitor controls the motor, in accordance with the position of the up/down switch, to drive the plunger 106 either upwardly or downwardly through the cylinder 104.

The balance of the circuit, as generally shown in FIG. 8A, is responsive to signals from the cell/barrier sensor 84, which comprises four piezo-resistive sensing elements 152a–d diffused in a diaphragm and connected in a Wheatstone bridge configuration, to automatically place the distal end of the probe 82 at the blood mixture interface 30 during a sampling operation, irrespective of the height or location of the interface within the test tube 20. Included is a power supply 154 for the cell/barrier sensor, which has a transformer 156 for supplying a stepped-down voltage to inputs to a diode bridge 158. Outputs from the diode bridge are connected to inputs to a regulator 160, such as a Motorola MC7815 regulator, as well as across a capacitor 162, which together provide positive and negative d.c. operating voltages for the sensor.

Also included is a power supply, indicated generally at 164, for converting line voltage to positive and negative d.c. voltages to operate a solid state relay 166, such as a Hamlin 7591 relay, which in turn controls a relay 168 having contacts 168a–c in the circuits for the motors 38, 50 and 94 to prevent operation of the motors when the relay 168 is energized. The power supply has a transformer 170 which provides a stepped-down voltage to a pair of diodes 172 and 174 connected with regulators 176 and 178 which may be, respectively, Motorola MC7912 and MC7812 regulators. Capacitors 180 and 182 operate as filters and capacitors 184 and 186 inhibit electrical noise at the outputs from the regulators.

The output signal from the cell/barrier sensor 84, at the juncture of the piezo-resistive elements 152a and 152d, has a value in accordance with the magnitude of pressure applied to the sensor, and is coupled to an inverting input to an operational amplifier (op amp) 188, a noninverting input to which receives an offset voltage controlled by the setting of a potentiometer 190. The output from the op amp is applied to a noninverting input to an op amp 192, the output from which is coupled through a diode 194 and a pair of Schmitt triggers 196 and 198 to the gate of a silicon controlled rectifier (SCR) 200. The anode of the SCR is connected to one input to the solid state relay 166, the other input to which is coupled with the output from a regulator 202, such as a Motorola MC7805 regulator, through a normally closed reset switch 204, and a capacitor 205 is connected between the gate and cathode of the SCR for noise suppression purposes. Upon occurence of an appropriate signal at the output from the op amp 192, the SCR is triggered into conduction to actuate the solid state relay and energize the relay 168. When the relay 168 is energized, all of its contacts 168a–c are opened to inhibit operation of any of the motors 38, 50 and 94, until the reset switch 204 is momentarily opened to interrupt conduction of the SCR when the signal is no longer present at the output from the op amp 192.

Because the sensor 84, i.e., one embodying the teachings of said U.S. Pat. No. 3,654,579, is an absolute pressure transducer, it is necessary to adjust the circuit to compensate for the effect of local atmospheric pressure on the sensor. Essentially, the output signal from the sensor which results from local atmospheric pressure is subtracted by the circuit, so that is does not cause a corresponding output from the op amp 192. For convenience a visual adjustment is made, and to that end the output from the op amp 188 is applied to the base of a PNP transistor 206, which has a light emitting diode (LED) 208 in series with its emitter, and the output from the op amp 192 is applied to the base of an NPN transistor 210, having an LED 212 in series with its collector.

Compensation is accomplished by adjusting the potentiometer 190 to change the offset voltage at the non-inverting input to the op amp 188 until the LED 212 is illuminated, which indicates that the op amp 192 is providing a positive voltage to the transistor 210, and therefore to the SCR 200 to actuate the solid state relay 166 and illuminate an LED 214. The potentiometer is then adjusted in the opposite direction until the LED 212 is just extinguished, which indicates that the circuit is subtracting from the output of the op amp 192 the signal from the sensor 84 which is attributable to local atmospheric pressure. The reset switch 204 is then momentarily opened to deactuate the solid state relay and render the SCR nonconductive, whereupon the apparatus is ready to begin a sampling operation. If at any time the LED 208 is illuminated, that will indicate that the circuit is overcompensating in the negative direction by allowing the op amp 108 to apply a negative voltage to the base of the transistor 206, and the potentiometer 190 must then be readjusted until the LED 212 is illuminated and then just extinguished, as above described.

Considering operation of the apparatus during a sampling cycle, FIG. 1 illustrates its orientation, and FIGS. 8A and 8B the state of the circuit, at the beginning of the cycle, at which point all of the plates 36, 48 and 90 are in their upper positions. To begin, the power switch 120 and the switch 122 are closed, the switch 130 is set to the "down" position and the switch 132 is momentarily actuated to energize the motor 38 and drive the first plate 36 downwardly, which carries with it the second and third plates 48 and 90. This brings the foot 70 of the tube sensor 62 onto the top of the stopper 22, whereupon with continued downward movement of the plates, the tube sensor then moves into the tube sensor guide 60 against the urging of the spring 64, until the trigger 72 actuates the limit switch 74. Actuation of the limit switch deenergizes the motor to terminate further downward movement of the plates, with the limit switch 44 at this time serving as a backup to deenergize the motor in the event the limit switch 74 does not open. At this point, the lower portion of the apparatus is positioned as shown in FIG. 2.

Figure 3:
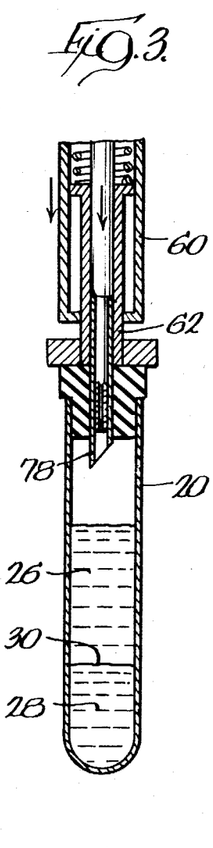

The next step is penetrating the stopper 22 with the needle 78, and to that end the switch 124 is closed, the switch 136 is set to the "down" position and the switch 138 is momentarily actuated to energize the motor 50 to drive the second plate 48, and with it the third plate 90, further downwardly. This forces the needle out of the tube sensor 62 and through the stopper as the tube sensor moves further into the tube sensor guide 60 against the urging of the spring 64, until the limit switch 56 is opened by its trigger 56a to deenergize the motor. The trigger is located so that, for a given height of test tube 20, the needle penetrates the stopper by a fixed distance, and at this point the configuration of the apparatus is as shown in FIG. 3.

Figure 4:
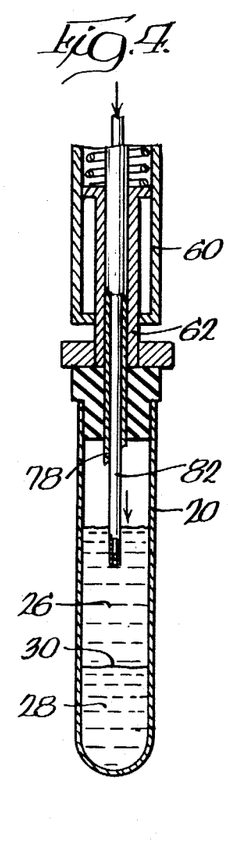

The probe or aspirator tube 82 is next extended through and out of the needle 78 and into and through the serum or liquid phase components of the blood mixture by closing th switch 126, setting the switch 142 to the "down" position and momentarily actuating the switch 144 to energize the motor 94 and drive the third plate 90 further downwardly. Extension of the probe through the serum, as shown in FIG. 4, continues until the distal end thereof, in which is contained the cell-/barrier sensor 84, contacts the cell coagulum or another separation barrier at the interface 30, as shown in FIG. 5. When contact is made with the interface, an increased pressure is placed on the sensor, causing it to generate a signal which appears at the output from the op amp 192 and triggers the SCR 200 to actuate the solid state relay 166. Actuation of the solid state relay energizes the relay 168 to open all of the contacts 168a-c, thereby inhibiting further operation of the motor 94, as well as any operation of the motors 38 and 50, to terminate downward movement of the probe and maintain the probe in fixed position. At this point, the openings 86 in the probe are positioned close to but slightly above the interface and entirely within the serum or liquid phase components 26 of the mixture.

A serum or plasma sample 216 of selected volume is then isolated from the mixture by closing the switch 128 and setting the switch 148 to the "up" position, which energizes the motor 112 to raise the plunger 106 and aspirate the serum through the openings 86 and the probe 82 into the cylinder 104. Aspiration continues until the trigger 118 engages the limit switch 114 to deenergize the motor, with the vertical setting of the limit switch determining the extent of upward movement of the plunger, and therefore the volume of the serum sampled.

It is to be appreciated that during the serum aspirating step, if not immediately after sensing the interface 30 and terminating further extension of the probe 82 into the mixture, the signal generated by the sensor 84 upon contact with the interface will be lost. If the solid state relay 166 depended for actuation upon the continued presence of the sensor signal, then upon loss of the signal the solid state relay and the relay 168 would deactuate and the contacts 168a-c would close, thereby reenergizing the motor 94 and driving the distal end of the probe beyond the interface and into the cell coagulum. This would result in the probe openings 86, instead of being positioned entirely within the serum for withdrawing a substantially particulate-free specimen, being moved into the cell coagulum. However, because of the SCR 200, the regulator 202 and the normally closed condition of the reset switch 204, once the solid state relay is triggered, it remains triggered despite a subsequent loss of sensor signal and until the reset switch is opened.

After the serum sample 216 is collected, the switch 142 is set to the "up" position and the reset switch 204 is momentarily opened to deactuate the solid state relay 166 and deenergize the relay 168 to return the contacts 168a-c to their normally closed position. Because downward movement of the plate 90 was terminated in response to contact of the distal end of the probe 82 with the interface 30, and not by movement of the plate to its lowermost position and opening of the limit switch 100, closure of the contact 168c energizes the motor 94 to move the plate upwardly and retract the probe back into the needle 78, until the limit switch 98 contacts its trigger 98a and deenergizes the motor. The switch 136 is then set to the "up" position and the switch 138 is momentarily actuated to energize the motor 50 and move the second plate 48, and with it the third plate 90, upwardly to withdraw the needle out of the stopper 22 and into the tube sensor 62, with the spring 64 at this time urging the tube sensor foot 70 against the stopper to push it off of the needle. Upward movement of the plates 48 and 90 continues until the limit switch 54 engages its trigger 54a to deenergize the motor 50, whereupon the switch 130 is set to the "up" position and the switch 132 is momentarily closed to energize the motor 38 and move all three plates 36, 48 and 90 upwardly until the limit switch 42 engages its trigger 42a. At this point, the apparatus is again oriented as shown in FIG. 1, except that the serum sample 216 is in the cylinder 104 and the plunger 106 is elevated therein.

To collect the serum sample for analysis, the test tube 20 is removed from the tray 24 and replaced with another vessel for receiving the sample. Switches 130 and 142 are then set to their "down" positions and switches 132 and 144 are momentarily closed to energize the motors 38 and 94. This moves the tube sensor 62 toward an open upper end of the vessel and extends the probe 82 into the vessel, with downward movement of the first and third plates 36 and 90 at this time being under control of the limit switches 44 and 100. The switch 148 is then placed in the "down" position to energize the motor 112 and drive the plunger 106 downwardly through the cylinder 104 to expel the serum sample through the probe openings 86 and into the vessel. The switches 130 and 142 are thereafter returned to their "up" positions and the switches 132 and 144 are momentarily actuated to return the apparatus to the orientation shown in FIG. 1.

To cleanse the apparatus in preparation for another sampling cycle, the vessel containing the collected serum sample is replaced with one containing flushing solution, for example distilled water. The switches 130 and 142 are then placed in their "down" positions and the switches 132 and 144 are momentarily actuated to extend the distal end of the probe 82 into the solution, whereupon the switch 148 is cycled between its "up" and "down" positions several times to move the plunger 106 up and down in the cylinder 104 to aspirate and expel flushing solution into and from the apparatus to cleanse the same of previously sampled serum. The switches 130 and 142 then placed in their "up" positions and the switches 132 and 144 are momentarily closed to again return the apparatus to the configuration shown in FIG. 1. At this point, the apparatus is prepared to commence a new sampling cycle, although if necessary or desired air may first be introduced through the needle and around the probe to dry the gap between the needle and probe.

The invention thus provides an improved method of and apparatus for isolating serum from cell coagulum of a blood mixture. Because of the cell/barrier sensor at the distal end of the probe, extension of the probe into the sample is precisely controlled, irrespective of the level of the interface, to ensure that the aspirator openings in the probe are always positioned above the interface and entirely within the serum, yet sufficiently close to the interface to ensure that substantially all of the serum is collected. At the same time, because movement of the probe into the mixture is precisely mechanically controlled, as compared with being manually extended therein, agitation of the mixture is kept to a minimum and the solid phase components are not disturbed and moved into the serum. In consequence, a particulate-free serum sample is obtained.

While one embodiment of the invention has been described in detail, various modifications and other embodiments thereof may be devised by one skilled in the art without departing from the spirit and scope of the invention, as defined in the appended claims.

What is claimed is:

1. Apparatus for isolating liquid phase components from semisolid phase components of a fluid mixture of the type in which the liquid phase components overlie the semisolid phase components and a liquid-semisolid interface is defined therebetween, comprising a probe; means for moving an end of said probe into and through the liquid phase components and toward and to the interface; means on said probe for sensing a change in pressure on said end of said probe upon said end contacting the interface and for generating a signal in response thereto; means for terminating movement of said probe upon generation of said signal, said probe having an opening therein close to but spaced from said end thereof so that said opening is located close to but spaced from the interface and entirely in the liquid phase components when said end reaches the interface; and means for withdrawing liquid phase components through said opening and probe after termination of movement of said probe.

2. Apparatus as in claim 1, including means for adjusting said sensing and generating means so that said signal is generated only in response to sensing at least a selected change in pressure on said probe end.

3. Apparatus as in claim 1, wherein said means for sensing and generating includes a pressure transducer carried by said probe for detecting an increase in pressure on said probe end upon said end contacting the interface.

4. Apparatus as in claim 1, wherein the fluid mixture is a biological fluid, said means for sensing and generating includes a pressure transducer carried by said probe close to said end thereof for detecting contact of said probe end with the interface, said pressure transducer being between said opening and said probe end.

5. Apparatus as in claim 4 wherein said probe is tubular and has a passage therethrough, said pressure transducer is within and sealed with said probe passage close to said probe end for sensing a change in pressure on said probe end upon said end contacting the interface.

6. Apparatus as in claim 1, wherein said apparatus is for sampling a fluid mixture in a vessel closed by a puncturable closure and said probe is tubular, and including a needle having a passage therethrough and a sharp end; means mounting said probe for movement by said probe moving means within and through said needle passage; and means for moving said needle sharp end against the closure to pierce the closure and extend said needle sharp end through the closure and into the vessel, said probe moving means, after said needle pierces the closure, moving said probe through said needle passage to move said probe end into and through the liquid phase components and toward and to the interface.

7. Apparatus as in claim 6 wherein, after operation of said withdrawing means, said probe moving means moves said probe end out of the vessel and into said needle passage and said needle moving means then moves said needle away from the closure to withdraw said needle from the closure.

8. Apparatus as in claim 6, wherein said means for withdrawing includes means for aspirating liquid phase components from the vessel through said probe opening and probe.

9. Apparatus as in claim 8, wherein said means for aspirating includes syringe means coupled with an opposite end of said probe.

10. A method of isolating liquid phase components from semisolid phase components of a fluid mixture of the type in which the liquid phase components overlie the semisolid phase components and a liquid-semisolid interface is defined therebetween, comprising the steps of moving an end of a probe into and through the liquid phase components and toward and to the interface; sensing a change in pressure on the end of the probe upon the end contacting the interface and generating a signal in response thereto; interrupting said moving step upon the signal being generated; and, after occurrence of said interrupting step, withdrawing liquid phase components through an opening in the probe close to but spaced from the end thereof and positioned entirely within the liquid phase components when the probe end reaches the interface.

11. A method as in claim 10, including the step of controlling the sensitivity of said sensing and generating step so that the signal is generated only in response to sensing at least a selected change in pressure on the probe end.

12. A method as in claim 10, wherein said sensing and generating step comprises sensing an increase in pressure at the probe end upon the end contacting the interface.

13. A method as in claim 10, wherein the probe is tubular and has a passage therethrough and the opening in the probe communicates with the passage, and including the step of sealing the passage at a point between the probe opening and probe end, and wherein said sensing and generating step comprises detecting a change in pressure at the sealed point in the probe passage upon the probe end contacting the surface.

14. A method as in claim 10, wherein the fluid mixture is in a vessel closed by a puncturable closure and the probe is tubular, and including the step of moving a needle, having a passage therethrough and a sharp end, sharp end first against the closure to pierce the closure and extend the needle sharp end through the closure and into the vessel, and wherein said probe moving step comprises moving the probe within and through the needle passage, after the needle pierces the closure, to move the probe end out of the needle beyond the needle sharp end and into and through the liquid phase components and toward and to the interface.

15. A method as in claim 14, wherein said withdrawing step comprises aspirating liquid phase components from the vessel through the probe opening and probe.

16. A method as in claim 15, wherein said aspirating step includes the step of generating a vacuum in a collection container coupled with an opposite end of the probe to aspirate liquid phase components into the container.

17. A method as in claim 14, including the steps, after said withdrawing step, of moving the probe end back into the needle passage, and thereafter moving the needle away from the closure to withdraw the needle from the closure.

18. A method as in claim 17, including the further steps, after the steps of moving the probe end back into the needle passage and moving the needle to withdraw the same from the closure, of again moving the probe to extend the probe end out of the needle passage beyond the needle sharp end, and thereafter expelling the withdrawn liquid phase components from the probe and probe opening into a receiving vessel.

19. A method as in claim 18, including the steps, after the expelling step, of extending the probe end and opening therein into a flushing solution, withdrawing flushing solution through the probe opening and probe, and then expelling the flushing solution from the probe and probe opening to clean the probe of liquid phase components.

* * * * *